US012702547B2

(12) United States Patent
Heniford et al.

(10) Patent No.: US 12,702,547 B2
(45) Date of Patent: Aug. 11, 2026

(54) HEART VALVE PROSTHESIS, ARTIFICIAL VALVE FORMED BY SAME, AND PREPARATION METHOD THEREFOR

(71) Applicant: Shanqian (Zhuhai) Biomaterials Technology Co., Ltd., Guangdong (CN)

(72) Inventors: Ryan Heniford, Guangdong (CN); Jiahua Xiao, Guangdong (CN)

(73) Assignee: Shanqian (Zhuhai) Biomaterials Technology Co., Ltd., Guangdong (CN)

( * ) Notice: Subject to any disclaimer, the term of this patent is extended or adjusted under 35 U.S.C. 154(b) by 929 days.

(21) Appl. No.: 17/919,405

(22) PCT Filed: Apr. 16, 2021

(86) PCT No.: PCT/CN2021/087826
§ 371 (c)(1),
(2) Date: Feb. 13, 2023

(87) PCT Pub. No.: WO2021/209046
PCT Pub. Date: Oct. 21, 2021

(65) Prior Publication Data

US 2023/0172708 A1 Jun. 8, 2023

(30) Foreign Application Priority Data

Apr. 17, 2020 (CN) ......................... 202010306006.7

(51) Int. Cl.
*A61F 2/24* (2006.01)

(52) U.S. Cl.
CPC ................................. *A61F 2/2415* (2013.01)

(58) Field of Classification Search
CPC .. A61F 2/2415; A61F 2/2412; A61L 2430/20; A61L 27/16; A61L 27/18; A61L 27/50
See application file for complete search history.

(56) References Cited

U.S. PATENT DOCUMENTS

2005/0177227 A1 8/2005 Heim et al.
2006/0235511 A1 10/2006 Osborne
(Continued)

FOREIGN PATENT DOCUMENTS

AU 2009295960 A1 4/2010
CA 2947049 A1 11/2015
(Continued)

OTHER PUBLICATIONS

International Search Report and Written Opinion dated Jul. 19, 2021; International Application No. PCT/CN2021/087826.
(Continued)

*Primary Examiner* — Suzette J Gherbi
(74) *Attorney, Agent, or Firm* — DINSMORE & SHOHL LLP

(57) ABSTRACT

A heart valve prosthesis includes a support element of a tubular structure, and at least two lobule bodies connected to the inner wall of the support element, wherein the support element comprises an outer layer fabric having selvages on opposite sides, and a suture line for fixing the other two sides of the outer layer fabric to each other to form the tubular structure; each of the lobule bodies is formed by stacking at least one lobule layer; and the opposite sides of the lobule body are respectively an interwoven side and a free side, with the interwoven side being fixed between the two selvages of the outer layer fabric by means of weaving, and the free side being a selvage. An artificial valve formed by same, and a preparation method therefor are also disclosed.

19 Claims, 5 Drawing Sheets

(56) References Cited

U.S. PATENT DOCUMENTS

| | | | | |
|---|---|---|---|---|
| 2010/0174359 | A1* | 7/2010 | Hefti | A61F 2/2412 606/139 |
| 2012/0095482 | A1* | 4/2012 | Peterson | A61F 2/0063 606/151 |
| 2012/0172978 | A1 | 7/2012 | DuMontelle | |
| 2017/0065408 | A1 | 3/2017 | Grundeman et al. | |
| 2017/0065411 | A1* | 3/2017 | Grundeman | A61F 2/2415 |
| 2018/0185143 | A1 | 7/2018 | Fish et al. | |
| 2019/0269507 | A1 | 9/2019 | Coe | |

FOREIGN PATENT DOCUMENTS

| | | | |
|---|---|---|---|
| CN | 106456326 | A | 2/2017 |
| CN | 106535824 | A | 3/2017 |
| CN | 106572906 | A | 4/2017 |
| CN | 106572907 | A | 4/2017 |
| CN | 212913479 | U | 4/2021 |
| CN | 212940074 | U | 4/2021 |
| JP | 2002200176 | A | 7/2002 |
| JP | 2012504031 | A5 | 2/2012 |
| JP | 2017517301 | A | 6/2017 |
| JP | 2017514584 | B2 | 8/2017 |
| WO | 2015169868 | A1 | 11/2015 |

OTHER PUBLICATIONS

First Office Action of Corresponding Japanese Application No. 2022-563216 dated Oct. 24, 2023, 13 pages.

Second Office Action of Corresponding Japanese Application No. 2022-563216 dated Mar. 6, 2024, 6 pages.

EP Search Report of Corresponding European Patent Application No. 21788092.1 dated Sep. 20, 2023, 8 pages.

* cited by examiner

HEART VALVE PROSTHESIS, ARTIFICIAL VALVE FORMED BY SAME, AND PREPARATION METHOD THEREFOR

CROSS-REFERENCE TO RELATED APPLICATIONS

This application is the U.S. National Stage of PCT/CN2021/087826 filed on Apr. 16, 2021, which claims priority to Chinese Patent Application 202010306006.7 filed on Apr. 17, 2020, the entire content of both are incorporated herein by reference in their entirety.

FIELD OF THE INVENTION

The present application relates to the field of medical instruments, in particular to a heart valve prosthesis, an artificial valve formed by the same, and a preparation method therefor.

BACKGROUND OF THE INVENTION

At present, three types of artificial valves, including 1) mechanical valves, 2) biological valves, and 3) synthetic polymer valves, are used in valve surgery.

Each of the mechanical valves consists of one or more valves mounted on an eccentric shaft and then fixed to a safety valve seat on heart muscle. These mechanical valves are extremely high in operation reliability, but easily cause blood disorder, thereby increasing the risk of thrombosis. Therefore, if a mechanical valve is implanted, a patient has to take an anticoagulant all his life; moreover, a valve assembly of the mechanical valve cannot be sufficiently compressed into a catheter, and thus cannot be delivered to a mounting location via the catheter in a minimal invasion way. Therefore, the mechanical valve has to be implanted by means of an open-heart surgery extremely strong in invasiveness so as not to be used by many senile patients suffering from comorbidity.

The biological valves are valve prosthesis prepared from human organ tissues (homografts) or animal-derived tissues (autografts). Generally, biological tissues of these valve prostheses may be favorably combined with the heart, and the biological valves have the additional advantage of supporting transcatheter delivery, so that the biological valves can overcome above-mentioned defects of the mechanical valves, thereby being more widely applied. However, the biological valves consist of organic tissues, and therefore, natural aging and degradation are easily caused. In order to avoid natural aging and degradation, generally, these biological tissues are required to be subjected to a lot of chemical treatment to guarantee the biocompatibility and avoid surface calcification. Moreover, these biological tissues can be effectively fixed in the heart only when being mounted on a seat, and the arrangement of such a seat may also cause disadvantageous flow conditions inside the biological valves.

The synthetic polymer valves, i.e., entire valve prostheses made of a synthetic material, are generally molded by using polyurethane or silica gel. These molded valves can effectively overcome problems relevant to material fatigue and also keep natural blood flow. However, as time goes on, there is a risk that these synthetic polymer valves are fracted in bent areas due to cyclic stress. In recent years, with the development of a three-dimensional printing technology, trials in the art are further increased, that is, shapes of native heart valves are copied by using various printable polymers in a more and more precise way. However, due to restrictions on product design and structural material, clinical or commercial success of these valves has hardly been made so far. Based on the cyclic stress, people have tried to prepare a "full-textile" heart prosthesis for many times by using a weaving technology, however, there is still a problem in the full-textile heart prosthesis disclosed in the prior art that the prosthesis is disabled due to overfatigue in the bent areas or the material and the shape cannot satisfy requirements.

For example, in an artificial valve described in an American literature US2012/0172978, a lobule body is formed alone by a single layer of screened material, that is, a formation process of the lobule body includes: cutting off the lobule body from the screened material, then finishing the lobule body to ensure that no any fibers extend out of an edge, and then, connecting the lobule body to a suture ring or a suture stent. The lobule body is cut off from the screened material, which causes more thread ends on the edge of the lobule body; and a post-connection suture way is adopted between the lobule body and the suture ring or the suture stent, by which the artificial valve having such a structure is affected by cut edges of a fabric or the existence of intersection points of suture lines, and thus, a prosthesis is disabled due to overfatigue in a bent area.

For another example, an artificial valve disclosed in a Chinese literature CN106535824 has a preparation process that: a single-layer fabric having selvages on two opposite sides is adopted; the selvages are edges 5 and 4 recorded in the literature; the single-layer fabric is folded in half in a direction where the selvages are located to form a two-layer structure, and the edges 5 and 4 of the two-layer structure are sutured by adopting two suture lines 22, wherein the suturing method includes: performing suturing in the radial direction of a stuffing yarn 11, and then, mutually suturing other two opposite sides except the edges 5 and 4 in the two-layer structure to form a cylinder-like structure. An inner layer fabric in the two-layer structure forms a lobule body, and an outer layer fabric forms a suture ring. There are the following defects in the design of the entire structure: firstly, three groups of suture lines are adopted in the structure, and due to the arrangement of the three groups of suture lines, the risk of fatigue damage is increased; secondly, the lobule body and the suture ring are both made of the same single-layer fabric, which results in that the lobule body and the suture ring can be only made of the same material, but properties required by the valve and the lobule body are different due to a stress effect generated during pulsatile flow, and therefore, the design for the same material cannot satisfy a requirement; and thirdly, due to structural restrictions, the connection between the lobule body and the suture ring may only be a rectilinear seam, and the lobule body may have and may only have one shape. Therefore, for the artificial valve disclosed in the literature, the seam of the lobule body cannot be created by a specific geometrical shape, and therefore, the design requirement of the lobule body of the valve having a specific shape cannot be satisfied.

SUMMARY OF THE INVENTION

The technical problem to be solved by the present application lies in that there is still a problem in a full-texture heart prosthesis disclosed in the prior art that the prosthesis is disabled due to overfatigue in the bent areas or the material and the shape cannot satisfy requirements, and thus, a heart valve prosthesis, an artificial valve formed by the same, and a preparation method therefor are provided.

According to one aspect of the present application, provided is a heart valve prosthesis, including a support element of a tubular structure, and at least two lobule bodies connected to the inner wall of the support element;

the support element includes an outer layer fabric having selvages on two opposite sides, and a suture line for fixing the other two sides of the outer layer fabric to each other to form the tubular structure; and each of the lobule bodies is formed by stacking at least one lobule layer; and two opposite sides of the lobule body are respectively an interwoven side and a free side, with the interwoven side being fixed between the two selvages of the outer layer fabric by means of weaving, and the free side being a selvage.

Preferably, each of the lobule layers is formed by interweaving an inner side warp and an inner side weft; the interwoven side of the lobule body is fixed by means of interweaving the inner side weft of each of the lobule layers onto the outer layer fabric; and the inner side warp is woven on the inner side weft.

Preferably, the number of yarns forming the inner side weft of each of the lobule layers is one; and the number of yarns forming the inner side warp of each of the lobule layers is also set to be one.

Preferably, the number of yarns forming the inner side weft in each of the lobule bodies is not greater than the number of the lobule layers in each of the lobule bodies; or/and the number of yarns forming the inner side warp in each of the lobule bodies is not greater than the number of the lobule layers in each of the lobule bodies.

Preferably, the number of yarns forming all the inner side wefts in all the lobule bodies is not greater than the number of the lobule bodies; or/and the number of yarns forming all the inner side warps in all the lobule bodies is not greater than the number of the lobule bodies.

Preferably, the number of yarns forming all the inner side warps in all the lobule bodies is set to be one, or/and the number of yarns forming all the inner side wefts in all the lobule bodies is set to be one.

Preferably, the number of yarns forming the inner side warps and the inner side wefts is set to be one in total.

Preferably, an interweaving area between each of the lobule bodies and the outer layer fabric is arc-shaped, rectilinear or/and of an irregular geometrical shape on a plane of the outer layer fabric.

Preferably, the support element and/or the lobule bodies are made of a biocompatible polymer.

Preferably, the lobule bodies are made of one or more of UHMWPE, PET, PEEK, TPU, PGA, PLGA, PLA, PLLA's, PDO, PHA's, and PGSU.

Preferably, the support element is made of one or more of UHMWPE, PET, PEEK, TPU, PGA, PLGA, PLA, PLLA's, PDO, PHA's, and PGSU.

Preferably, the length of the support element in the axial direction is 1 mm to 50 mm, and the yarns forming the outer layer fabric have the sizes of 5-100 D.

According to another aspect of the present application, provided is a preparation method for the heart valve prosthesis, including:

step 1, adopting a plurality of yarns to be arranged to form outer side warps, and adopting one yarn as an outer side weft to be interwoven with the outer side warps to form an outer layer fabric, two opposite sides, parallel to the outer side warps, of the outer layer fabric forming selvages;

step 2, disposing a plurality of grab ropes above the outer layer fabric, providing an interweaving area on the outer layer fabric, selecting one yarn to be interwoven with at least one outer side warp on one side of the interweaving area firstly, then extending to one of the grab ropes where the yarn is fixed, and then returning to the interweaving area, wherein the process of fixation between the interweaving area and one of the grab ropes is repeated until the yarn forms an inner side weft of each lobule layer after the yarn completes all areas from one side of the interweaving area to one side of each of the grab ropes; the side fixed to the grab rope being a free side of the inner side weft;

step 3, adopting another yarn as an inner side warp to be interwoven on the inner side weft to form an inner side warp of each of the lobule layers; and using a thread end of the inner side warp to weave a plurality of lobule layers into a whole on the free side of the inner side weft to form individual lobule bodies; and step 4, after all the lobule bodies are woven completely, suturing two axial ends of each of the outer side warps on the outer layer fabric by using a suture line.

Preferably, in step 3, the thread end of the inner side warp returns to a location adjacent to the interweaving area so as to be ligated after being sequentially overlocked with the inner side weft on the free side of the inner side weft.

Preferably, in step 1, the number of the yarns arranged to form the outer side warps is one.

According to further aspect of the present application, provided is a preparation method for the heart valve prosthesis, including:

step 1, adopting a plurality of yarns to be arranged to form outer side warps, providing an interweaving area on the outer side warps, disposing a plurality of grab ropes above the outer side warps, adopting one yarn as an outer side weft to be interwoven with the outer side warps, fixing the yarn forming the outer side weft to one of the grab ropes when being interwoven to the interweaving area, and then, returning the yarn to the interweaving area so as to be further interwoven with the outer side warps; making the yarn forming the outer side weft cooperate with the outer side warps to form an outer layer fabric, fixing the yarn forming the outer side weft to one of the grab ropes after extending to one of the grab ropes when being in the interweaving area, and then, returning the yarn to the outer side warps so that the yarn forming the outer side weft forms an inner side weft at segments between each of the outer side warps and each of the grab ropes; the side fixed to the grab rope being a free side of the inner side weft;

step 2, adopting another yarn as an inner side warp to be interwoven on the inner side weft to form an inner side warp of each of lobule layers; and using a thread end of the inner side warp to weave a plurality of lobule layers into a whole on the free side of the inner side weft to form individual lobule bodies; and step 3, after all the lobule bodies are woven completely, suturing two axial ends of each of the outer side warps on the outer layer fabric by using a suture line.

According to yet further aspect of the present application, provided is an artificial valve, including the above-mentioned heart valve prosthesis or the heart valve prosthesis prepared by using the above-mentioned preparation method, and a stent mounted on the heart valve prosthesis.

The technical solutions of the present application have the following advantages.

1. According to the present application, due to the adoption of the way that the two opposite sides of each of the lobule bodies are respectively set as the interwoven side and the free side and the interwoven side is fixed between the two selvages of the outer layer fabric by means of weaving, the edge on the interwoven side of each of the lobule bodies can be seamlessly woven and fixed to the outer layer fabric; the free side of each of the lobule bodies is set as the selvage, so that the number of the suture lines in the heart valve prosthesis is effectively reduced to one only for fixing the outer layer fabric to form the tubular structure; and the suture line is disposed on a radial location of the support element, thereby having less influence from a stress generated during pulsatile flow. Meanwhile, there are no cut edges of a fabric on locations except a location where the suture line is located, so that the problems of inherent stress concentration and compliance mismatching of a valve suturing technology are reduced. Therefore, the heart valve prosthesis in the present application is not prone to generation of stress fatigue, and then, the heart valve prosthesis in the present application can be better prevented from being disabled, thereby prolonging the service life effectively.

In addition, each of the lobule bodies is designed independent from the support element, and therefore, the materials for the support element and the lobule bodies can be set to be different. A composition of various materials can be used for optimization to form ideal flow dynamics, and then, the requirement of the stress generated during pulsatile flow on the material properties of the valve and the lobule bodies is satisfied.

Meanwhile, the shape of the interweaving area between each of the lobule bodies and the support element can be voluntarily designed, and this area can be set to be rectilinear or of other specific geometrical shapes. Furthermore, the lobule bodies and the support element are respectively formed by separate weaving, so that the shapes of the lobule bodies can change according to design requirements, and the number of the lobule layers forming the lobule bodies can also be voluntarily adjusted as required, for example, the number of the lobule layers forming single lobule body may be set to be one or more. When the plurality of lobule layers are set, the distances from the interwoven sides to the free sides of the plurality of lobule layers can be increased or reduced layer by layer, and thus, a gradient thickness is effectively formed. In summary, according to the present application, the shapes of the lobule bodies can be designed to be more diversified, and thus, the heart valve prosthesis in the present application adapts to the design of any number of lobule bodies having any geometrical shapes; and when these geometrical shapes cooperate with materials having various components, a more ideal flow dynamics effect can be obtained specifically.

2. According to the present application, the number of the yarns forming the lobule bodies is further optimized. The number of the yarns forming the inner side warp and the inner side weft and adopted in the processes of weaving single lobule layer, single lobule body and a plurality of lobule bodies may be set to be one or more, and it is only required that the thread ends of the one or more woven yarns are located on two ends of the interweaving area between the single lobule body and the outer layer fabric. In the present application, preferably, the number of the yarns forming the inner side warp and the inner side weft in each of the lobule bodies is respectively set to be one; and by such setting, it is convenient to better interweave the lobule bodies, and the weaving method is simplified. Furthermore, by setting the structure of the heart valve prosthesis, the stent is also potentially allowed to be rapidly put on an interface of two adjacent lobule bodies between the lobule bodies and the support element and is more accurately and more rapidly assembled, with less subjectivity, on the lobule bodies and components of the support element.

3. By using the preparation method adopted in the present application, the heart valve prosthesis only having one suture line and having no cut edges except the location of the suture line can be effectively prepared. The preparation method is applicable to an existing manufacturing device, not only can effectively overcome the defect of poor anti-fatigue effect of the existing heart valve prosthesis, but also can prepare the lobule bodies having different shapes so that the design requirement on the shapes of the lobule bodies is satisfied; and the method in the present application can be used for preparation by using an existing weaving device frequently used in the field of medical devices.

BRIEF DESCRIPTION OF THE DRAWINGS

In order to more clearly display structures of products in the present application, the present application also provides the following accompanying drawings.

DESCRIPTION FOR REFERENCE NUMERALS IN THE ACCOMPANYING DRAWINGS

1—support element,
2—lobule body,
3—grab rope;
12—outer layer fabric,
13—suture line;
21—inner side warp,
22—inner side weft.

DETAILED DESCRIPTION OF THE INVENTION

The following embodiments are provided for better further understanding the present application, but are not limited to the optimal implementations, and do not constitute limitations on the content and the protection scope of the present application. Any products which are the same or similar to those in the present application and derived under the inspiration of the present application or derived by combining features in the present application with features in the prior art shall fall within the protection scope of the present application.

Embodiment 1

Figure 1:
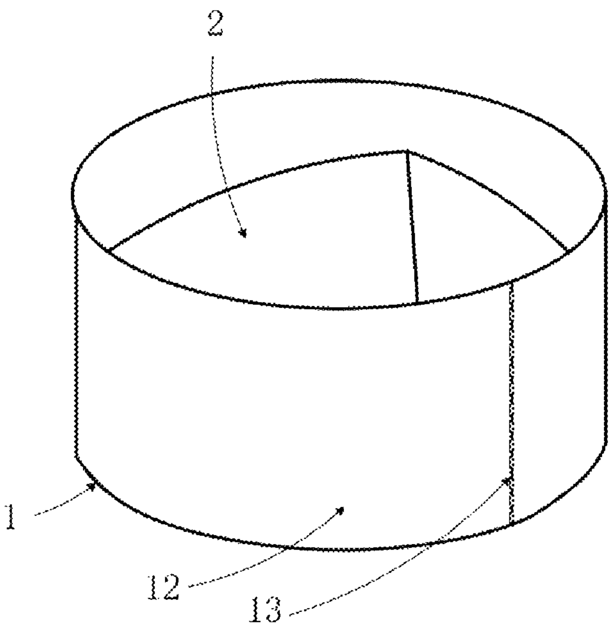
FIG. 1 is a schematic structural diagram of a heart valve prosthesis in the present application.

A heart valve prosthesis, as shown in FIG. 1, includes a support element 1 of a tubular structure, and, and a plurality of lobule bodies 2 connected to the inner wall of the support element 1; the support element 1 includes an outer layer fabric 12 having selvages on two opposite sides, and a suture line 13 for fixing the other two sides of the outer layer fabric 12 to each other to form the tubular structure; each of the lobule bodies 2 is formed by stacking a plurality of lobule layers; and two opposite sides of the lobule body 2 are respectively an interwoven side and a free side, with the interwoven side being fixed between the two selvages of the outer layer fabric 12 by means of weaving, and the free side being a selvage.

In the present application, the selvage is an edge formed after a warp loops back to a weaving area from a weft on the most edge and is further woven, or an edge formed after a weft loops back to a weaving area from a warp on the most edge and is further woven. There are no thread ends in the middle of the selvage, and the thread ends only exist on two ends of the edge which is woven completely.

In the present application, due to the adoption of the way that two opposite sides of each of the lobule bodies are respectively set as the interwoven side and the free side, that is, one side is set as the interwoven side, the other side opposite to the interwoven side is set as the free side, moreover, the interwoven side is fixed between the two selvages of the outer layer fabric by means of weaving, and the free side is set as the selvage, the edge on the interwoven side of the lobule body can be seamlessly woven and fixed to the outer layer fabric; the free side of the lobule body is set as the selvage, so that the number of the suture lines in the heart valve prosthesis is effectively reduced to one only for fixing the outer layer fabric to form the tubular structure. Moreover, the suture line is disposed on a radial location of the support element, thereby having less influence from a stress generated during pulsatile flow. Meanwhile, there are no cut edges of a fabric on locations except a location where the suture line is located, so that the problems of inherent stress concentration and compliance mismatching of a valve suturing technology are reduced. Therefore, the heart valve prosthesis in the present application is not prone to generation of stress fatigue, and then, the heart valve prosthesis in the present application can be better prevented from being disabled, thereby prolonging the service life effectively.

Furthermore, each of the lobule bodies is designed independent from the support element, and therefore, the materials for the support element and the lobule bodies can be set to be different. A composition of various materials can be used for optimization to form ideal flow dynamics, and then, the requirement of the stress generated during pulsatile flow on the material properties of the valve and the lobule bodies is satisfied.

Meanwhile, in the present application, the shape of the interweaving area between each of the lobule bodies and the support element can be voluntarily designed, and this area can be set to be rectilinear or of other specific geometrical shapes. Furthermore, the lobule bodies and the support element are respectively formed by separate weaving, so that the shapes of the lobule bodies can change according to design requirements, and the number of the lobule layers forming the lobule bodies can also be voluntarily adjusted as required, for example, the number of the lobule layers forming single lobule body may be set to be one or more. When the plurality of lobule layers are set, the distances from the interwoven sides to the free sides of the plurality of lobule layers can be increased or reduced layer by layer, and thus, a gradient thickness is effectively formed. In summary, according to the present application, the shapes of the lobule bodies can be designed to be more diversified, and thus, the heart valve prosthesis in the present application adapts to the design of any number of lobule bodies having any geometrical shapes; and when these geometrical shapes cooperate with materials having various components, a more ideal flow dynamics effect can be obtained specifically.

Figure 2:
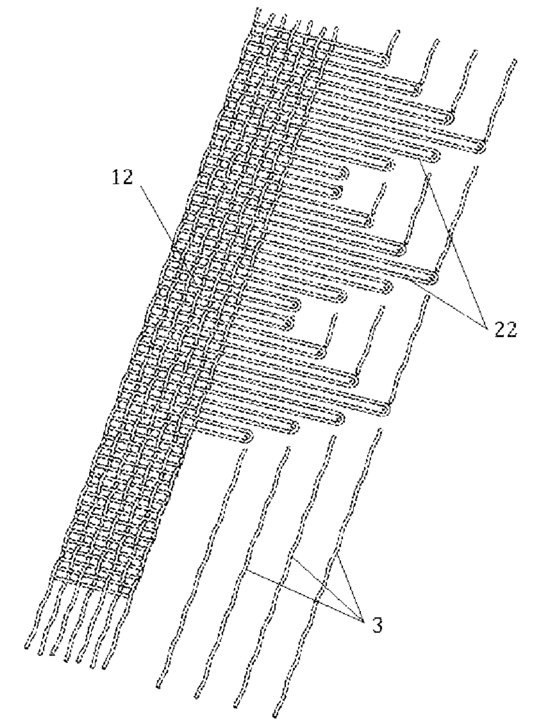
FIG. 2 is a schematic diagram showing a front structure obtained after an inner side weft is interwoven on an outer layer fabric in the present application.
Figure 3:
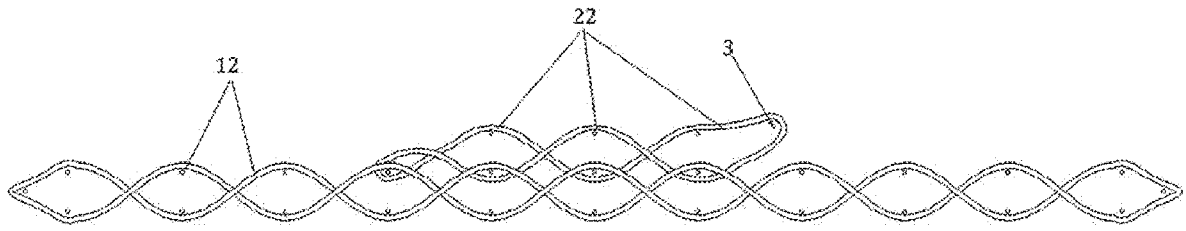
FIG. 3 is a schematic diagram showing a sectional structure obtained after the inner side weft is interwoven on the outer layer fabric in the present application.

In the present application, the number of the lobule bodies 2 may be set to be two or more. In the present application, the number of the lobule layers forming single lobule body 2 may be set to be one or more. In the present embodiment, the number of the lobule layers in each of the lobule bodies 2 is set to be one, and the number of the lobule bodies 2 is set to be three, as shown in FIG. 1 to FIG. 3. Moreover, in the present embodiment, each of the lobule layers is formed by interweaving an inner side warp 21 and an inner side weft 22. The interwoven side of each of the lobule bodies 2 is fixed by weaving the inner side weft 22 of each of the lobule layers onto the outer layer fabric 12. The inner side warp 21 is woven on the inner side weft 22. In the present embodiment, all the edges of the lobule bodies are selvages. In the present application, the outer layer fabric 12 is also formed by interweaving an outer side weft and outer side warps.

The above-mentioned interweaving mode is a conventional weaving mode, including, but not limited to 1×1, 1×2, 2×2, and 1×3. So-called 1×1 weaving mode refers to a weaving mode that an outer side weft is interwoven with an outer side warp, so-called 1×2 weaving mode refers to a weaving mode that an outer side weft is interwoven with two outer side warps, or two outer side wefts are interwoven with an outer side warp, and so on as long as it is an interweaving mode by which selvages can be formed on two opposite sides. In the present application, the outer layer fabric 12 and the lobule bodies 2 are woven by adopting any one or more of the above-mentioned weaving modes.

Figure 4:
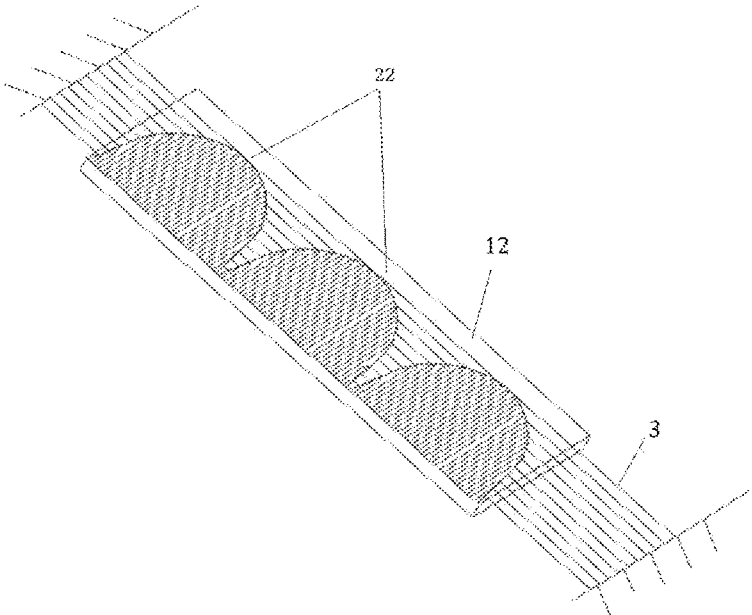
FIG. 4 is a schematic diagram showing a three-dimensional structure obtained after the inner side weft is interwoven on the outer layer fabric in the present application.
Figure 5:
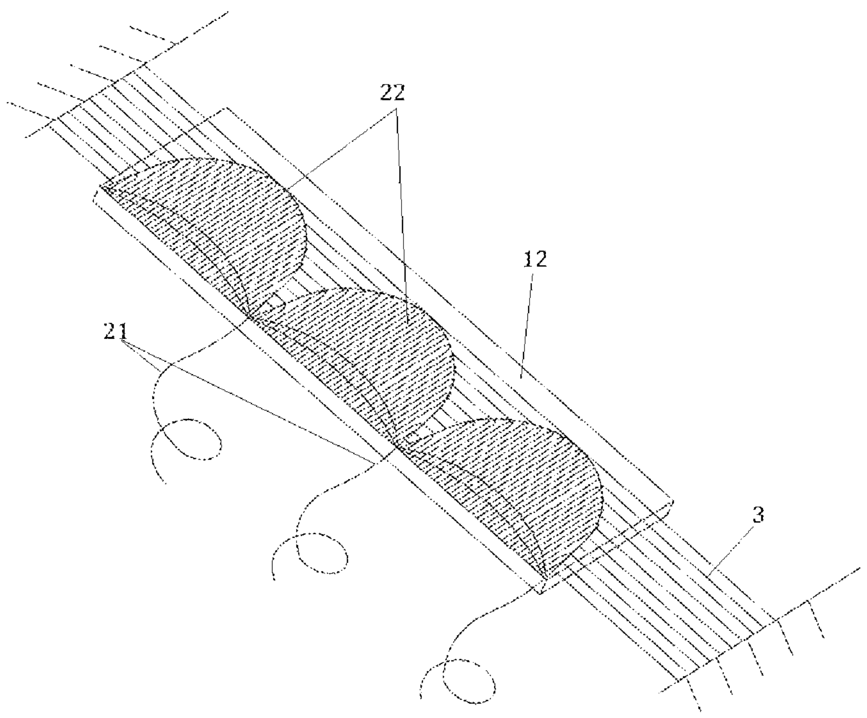
FIG. 5 is a schematic diagram showing a structure obtained after an inner side warp is interwoven on the inner side weft in the present application.
Figure 6:
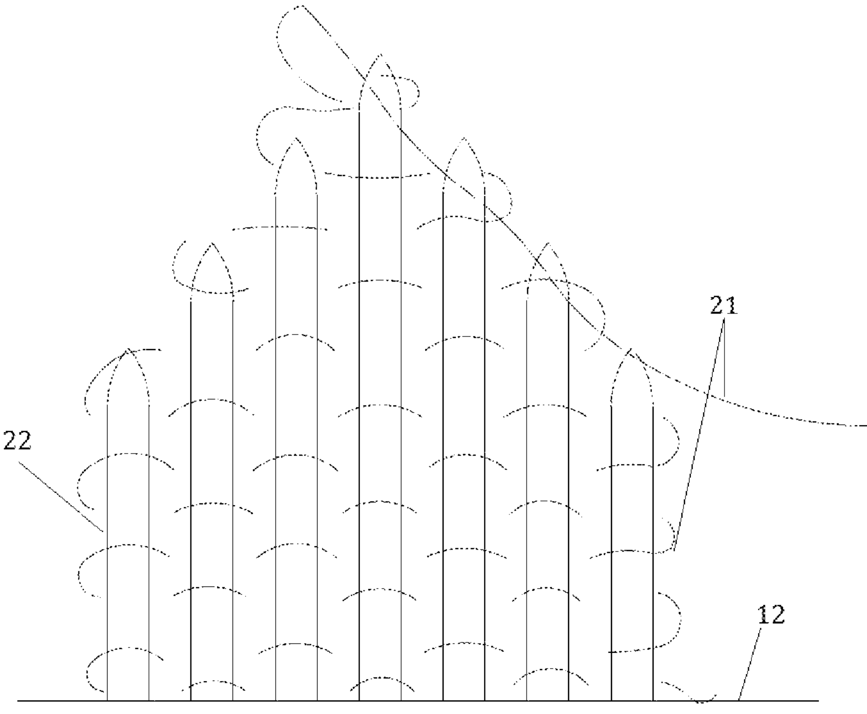
FIG. 6 is a schematic diagram showing a structure obtained after a yarn on the inner side warp loops back to an interweaving area in the present application.
Figure 7:
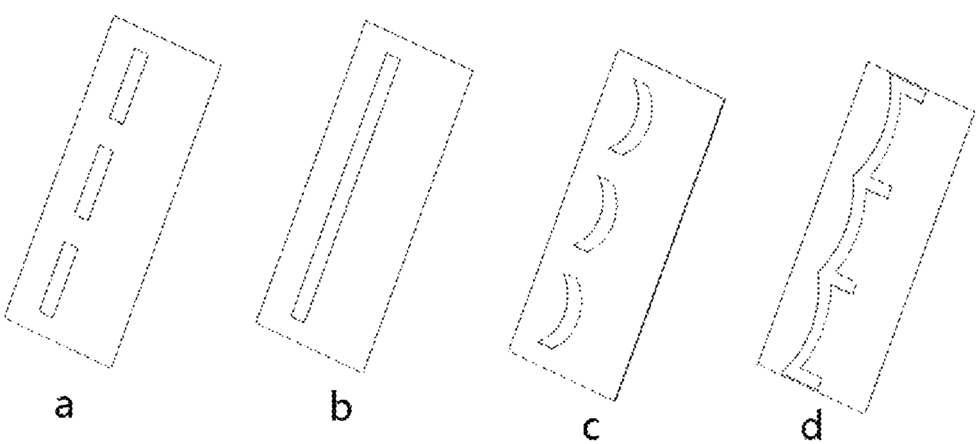
FIG. 7 is a schematic diagram showing a geometrical shape of the interweaving area between a lobule body and the outer layer fabric in the present application.
Figure 8:
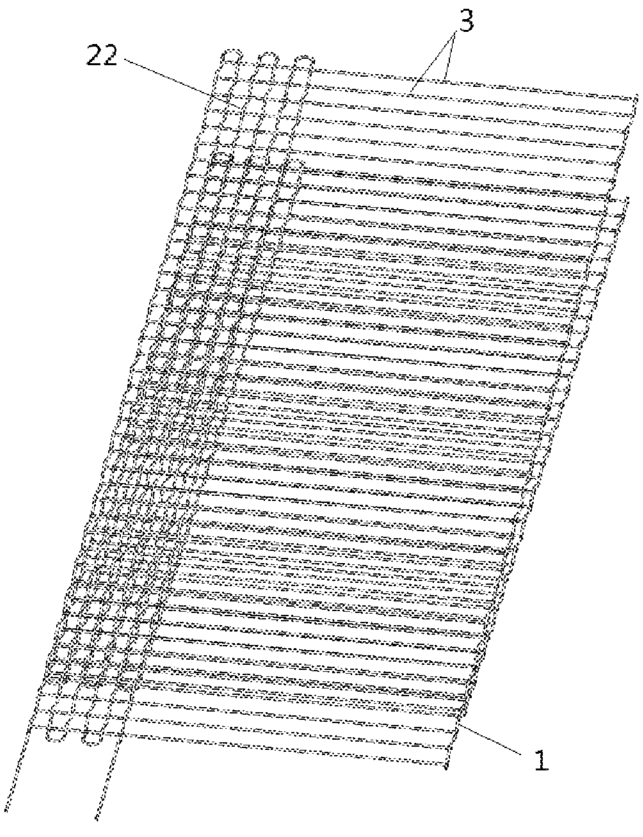
FIG. 8 is a schematic diagram showing a lateral structure of the inner side weft of the lobule body in a preparation method recorded in Embodiment 2.

In the present application, when the outer side weft is interwoven with the outer side warps, it is possible to only form the outer layer fabric 12, as shown in FIG. 4 and FIG. 7; or it is also possible to form the inner side weft 22 of the lobule body 2 by adopting the outer side weft of the outer layer fabric 12 while forming the outer layer fabric 12, as shown in FIG. 8. If the outer layer fabric 12 is only formed when the outer side weft and the outer side warps are interwoven, a new yarn may be adopted to be woven on the outer layer fabric 12 to form the inner side weft 22 of the lobule body 2; and if the inner side weft 22 is also woven by using the outer side weft when the outer side weft and the outer side warps are interwoven, a new yarn is only required to be used as the inner side warp 21 to be interwoven on the inner side weft 22 to form the lobule body 2. In the present embodiment, the mode adopted is that the outer layer fabric 12 is only formed when the outer side weft and the outer side warps are interwoven; then, a new yarn is adopted to be woven on the outer layer fabric 12 to form the inner side weft 22 of the lobule body 2; and subsequently, interweaving and stuffing are performed on the inner side weft 22 to form the inner side warp 21, and the inner side warp 21 and the inner side weft 22 are interwoven together to form the lobule body 2 having the selvages on all the edges, as shown in FIG. 2 to FIG. 6.

In the present embodiment, a yarn may be woven to form inner side wefts 22 of three lobule bodies 2, or three yarns are respectively woven to form the inner side wefts 22 of the three lobule bodies 2. The inner side warps 21 of the lobule bodies 2 may be formed by adopting yarns woven to form the inner side wefts 22 to be further interwoven on the inner side wefts 22, or may be formed by adopting new yarns to be further interwoven on the inner side wefts 22. That is, in the present application, the number of yarns forming all the inner side wefts 22 in all the lobule bodies 2 is not greater than the number of the lobule bodies 2; or/and the number of yarns forming all the inner side warps 21 in all the lobule bodies 2 is not greater than the number of the lobule bodies 2; preferably, the number of yarns forming all the inner side wefts 22 in all the lobule bodies 2 is set to be one, or/and the number of yarns forming all the inner side warps 21 in all the lobule bodies 2 is set to be one; and more preferably, the number of yarns forming the inner side warps 21 and the inner side wefts 22 is set to be one in total. In the present embodiment, the number of yarns forming all the inner side wefts 22 in all the lobule bodies 2 is set to be one, and the number of yarns forming all the inner side warps 21 in all the lobule bodies 2 is set to be three, as shown in FIG. 5 to FIG. 6.

In the present application, the support element 1 and/or the lobule bodies 2 are made of a biocompatible polymer. The lobule bodies are made of one or more of UHMWPE (ultra-high molecular weight polyethylene), PET (polyethylene terephthalate), PEEK (polyetheretherketone), TPU (thermoplastic polyurethane), PGA (polyglycolic acid), PLGA (poly (lactic-co-glycolic acid)), PLA (polylactic acid), PLLA's (poly-L-lactic acid), PDO (polydioxanone), PHA's (polyhydroxyalkanoate), and PGSU (poly (glycerol-sebacate) polyurethane); and the support element 1 is made of one or more of UHMWPE, PET, PEEK, TPU, PGA, PLGA, PLA, PLLA's, PDO, PHA's, and PGSU. In the present embodiment, the support element 1 is made of PET, and the lobule bodies 2 are made of UHMWPE. That is, the support element 1 is woven by using a yarn made of PET, and the lobule bodies 2 are woven by using a yarn made of UHMWPE.

In the present application, the geometrical shape of an interweaving area between each of the lobule bodies 2 and the outer layer fabric 12 may be adjusted according to situations, and the geometrical shape may be rectilinear or curved or of an irregular geometrical shape, as shown in FIG. 7 in which a and b are schematic diagrams showing the rectilinear shape, c is a schematic diagram showing the curved shape, and d is a schematic diagram showing the irregular geometrical shape. The width of the interweaving area may be determined according to the number of the outer side warps interwoven between each of the inner side wefts 22 and the outer layer fabric 12, and the number of the outer side warps interwoven with the inner side wefts 22 ranges from 2 to 50. The interweaving area between every two adjacent lobule bodies 2 may be continuous or discontinuous. In FIG. 7, a and c are schematic diagrams showing that the interweaving area is discontinuous, and b and d are schematic diagrams showing that the interweaving area is continuous. In the present embodiment, the interweaving area between every two adjacent lobule bodies 2 is continuous and arc-shaped.

Figure 9:
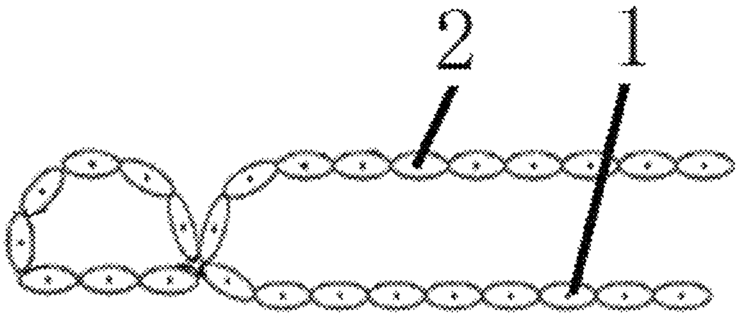
FIG. 9 is a schematic diagram showing a sectional structure that a selvage on the front edge of a support element is bent to be tubular in the present application.
Figure 10:
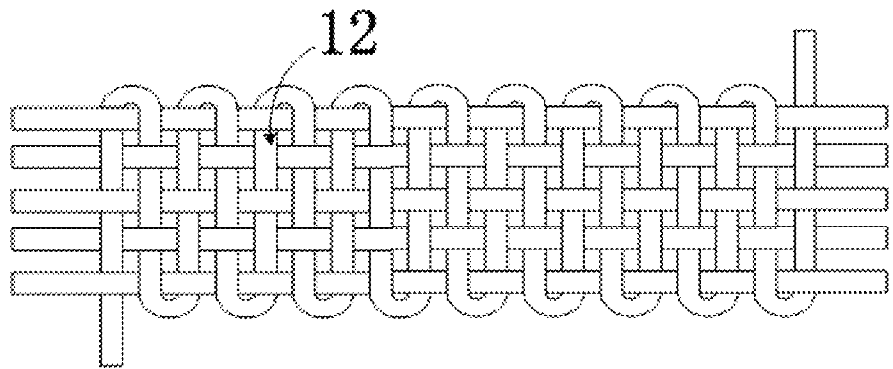
FIG. 10 is a schematic structural diagram of an outer layer fabric that is interwoven by adopting a 1×1 weaving mode in the present application.

In the present application, the length of the support element 1 in the axial direction may change within the range of 1 mm to 50 mm, and the sizes of the yarns forming the outer layer fabric 12 may also be set to be 5-100 D according to the requirement on thickness. A selvage on a front side of the tubular structure of the support element 1 may be bent in a direction facing the lobule bodies 2 to form another tubular structure, as shown in FIG. 9.

In the present embodiment, a preparation method for the above-mentioned heart valve prosthesis is described as follows.

In step 1, a plurality of yarns made of PET are adopted to be arranged to form outer side warps; one yarn made of PET is adopted as an outer side weft to be interwoven with the outer side warps in a 1×1 weaving mode to form an outer layer fabric 12; and two opposite sides, parallel to the outer side warps, of the outer layer fabric 12 form selvages.

In step 2, a plurality of grab ropes 3 are disposed above the outer layer fabric 12, as shown in FIG. 2; an interweaving area is determined on the outer layer fabric 12 along the outer side warps, and in the present embodiment, the interweaving area is selected to be rectilinear; and one yarn made of UHMWPE is selected to be interwoven with at least one outer side warp on one side of the interweaving area firstly, then extends to one of the grab ropes 3 where the yarn is fixed, as shown in FIG. 3, and then loops back to the interweaving area, wherein the process of fixation between the interweaving area and one of the grab ropes 3 is repeated until the yarn forms an inner side weft 22 of each lobule layer after the yarn completes all areas from one side of the interweaving area to one side of each of the grab ropes 3, as shown in FIG. 2 and FIG. 4. The shapes of the lobule bodies 2 and the perimeters of edges thereof are determined according to a location where the inner side weft 22 is fixed on the grab rope 3. In the present embodiment, when the lobule bodies are set to be semielliptic, a fixing point between the inner side weft 22 and the grab rope 3 is semielliptic, as shown in FIG. 2 and FIG. 4.

In step 3, another yarn made of UHMWPE is adopted as an inner side warp 21 to be interwoven on the inner side weft 22 to form a single lobule body 2; in the present step, in order to facilitate weaving, preferably, the grab rope 3 on each fixing point between the inner side weft 22 and the grab rope 3 forms a coil to be fixed on a loom under the condition that the tension on the location of the fixing point on the grab rope 3 and the tension of the grab rope 3 itself are maintained, and the loom fixes each coil on a raised or lowered location respectively; a 1×2 weaving mode is adopted, by which the yarn used as the inner side warp 21 is transferred back and forth among the free coils, as shown in FIG. 5 and FIG. 6, thereby being interwoven among the free coils until all the inner side wefts 22 are stuffed completely; and after the stuffing is completed, a thread end of the inner side warp 21 returns to a location where the outer layer fabric 12 is interwoven so as to be ligated after being sequentially overlocked with the inner side weft 22 on the free side of the inner side weft 22, as shown in FIG. 6, and the single lobule body 2 may be formed by adopting the above-mentioned weaving mode. For the lobule body 2 located in the middle, the inner side warp 21 of the lobule body 2 may also penetrate through the inner side weft 22 on a location adjacent to the lobule body 2 during weaving, and thus, seamless connection between the adjacent lobule bodies 2 is achieved. By changing the geometrical shape of an area between two adjacent lobule bodies 2, the flow characteristic of the heart valve prosthesis can be effectively optimized, or an anchorage point of a stent is allowed to be strengthened.

In the present application, it is also possible that an elastic fiber penetrates through a location where the grab rope 3 is fixed, that is, the elastic fiber penetrates through an annular ring of the inner side weft 22 on the fixing point of each grab rope 3; when the elastic fiber is in a tension state, the diameter of the elastic fiber can be remarkably reduced, so that the yarn forming the inner side warp 21 easily passes through the annular ring: when the tension is released, the diameter of the elastic fiber can be remarkably increased to stuff gaps left by the fixing point of the grab rope 3; and the elastic fiber transferred around the lobule bodies 2 may also play a sealing role, thereby improving the dynamics performance of blood of the lobule bodies 2. In the present embodiment, the number of the lobule bodies 2 is three, and therefore, it is only required that three lobule bodies 2 are woven completely according to the above-mentioned weaving mode. The grab ropes 3 are removed after all the lobule bodies 2 are woven completely, and then, the outer layer fabric 12 interwoven with the lobule bodies 2 is taken from the loom.

In step 4, two axial ends of each of the outer side warps on the outer layer fabric 12 are sutured by using a suture line 13, as shown in FIG. 1. In the present application, before the two ends of each of the outer side warps on the outer layer fabric 12 are sutured, it is also possible that a selvage on a front edge of the outer layer fabric 12 is fixed on the interweaving area of the outer layer fabric 12 after being bent to a direction where the lobule bodies 2 are located, as shown in FIG. 9.

Embodiment 2

The present embodiment provides another preparation method for the heart valve prosthesis. The structure of a prepared heart valve prosthesis is basically same as that in embodiment 1, except that the material of an inner side weft 22 in the present embodiment is the same as that of an outer layer fabric 12. In terms of the preparation method, the difference lies in that the inner side weft 22 is also woven by using an outer side weft while the outer side weft and outer side warps are interwoven. A specific preparation process is described as follows.

In step 1, a plurality of yarns made of PET are adopted to be arranged to form outer side warps; an interweaving area is disposed on the outer side warps; a plurality of grab ropes 3 are disposed above the outer side warps; one yarn made of PET is adopted as an outer side weft to be interwoven with the outer side warps; and the yarn forming the outer side weft is fixed to one of the grab ropes 3 when being interwoven to the interweaving area, and then, the yarn returns to the interweaving area so as to be further interwoven with the outer side warps, as shown in FIG. 8. The yarn forming the outer side weft cooperates with the outer side warps to form an outer layer fabric 12, and the yarn forming the outer side weft forms an inner side weft 22 at segments between the interweaving area and each of the grab ropes 3. That is, the yarn forming the outer side weft and the inner side weft 22 are formed by the same yarn.

In step 2, another yarn made of UHMWPE is adopted as an inner side warp 21 to be interwoven on the inner side weft 22 to form a lobule body 2. In the present step, in order to facilitate weaving, preferably, the grab rope 3 on each fixing point between the inner side weft 22 and the grab rope 3 forms a free coil to be fixed on a loom under the condition that the tension on the location of the fixing point on the grab rope 3 and the tension of the grab rope 3 itself are maintained, and the loom fixes each free coil on a raised or lowered location respectively; a 1×2 weaving mode is adopted, by which the yarn used as the inner side warp 21 is transferred back and forth among the free coils, as shown in FIG. 5 and FIG. 6, thereby being interwoven among the free coils until all the inner side wefts 22 are stuffed completely; and after the stuffing is completed, a thread end of the inner side warp 21 returns to a location where the outer layer fabric 12 is interwoven so as to be ligated after being sequentially overlocked with the inner side weft 22 on the free side of the inner side weft 22, as shown in FIG. 6, and the single lobule body 2 may be formed by adopting the above-mentioned weaving mode. In the present embodiment, the number of the lobule bodies 2 is three, and therefore, it is only required that three lobule bodies 2 are woven completely according to the above-mentioned weaving mode. The grab ropes 3 are removed after all the lobule bodies 2 are woven completely, and then, the outer layer fabric 12 interwoven with the lobule bodies 2 is taken from the loom.

In step 3, two axial ends of each of the outer side warps on the outer layer fabric 12 are sutured by using a suture line 13, as shown in FIG. 1.

Embodiment 3

An artificial valve includes the heart valve prosthesis prepared in embodiment 1 or embodiment 2 and further includes a stent mounted on the heart valve prosthesis. After being prepared, the heart valve prosthesis in the present embodiment may be processed by using any post-processing technologies such as thermal molding, embedded molding, ultrasonic welding, solvent treatment, and scouring (cleaning by using a solvent) to construct a final geometrical shape, and is fixed together with the stent after being constructed completely. The appropriate stent specially designed for a heart valve is fixed on a seamless connection location between a lobule body 2 and a support element 1. A method for fixing the stent on the heart valve prosthesis depends on the geometrical shape of the stent and the structure of the heart valve prosthesis, and a way for fixation between the heart valve prosthesis and the stent includes, but is not limited to suturing, welding, and adhesive bonding. By adopting the heart valve prosthesis provided in the present application, it is more convenient to align and locate the stent, and thus, the stent can be mounted more accurately and simply with lower subjectivity.

Embodiment 4

Provided is a heart valve prosthesis. The difference of the present embodiment and embodiment 1 lies in that lobule layers forming a lobule body 2 in the present embodiment are of multilayer structures and may be set to be of two-layer or three-layer or more-layer structures.

Figure 11:
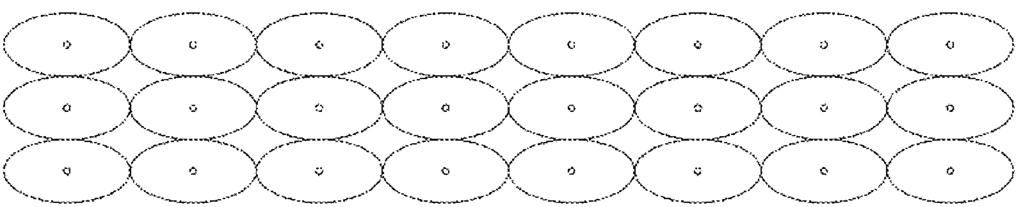
FIG. 11 is a side view I of a lobule body in the present application.
Figure 12:
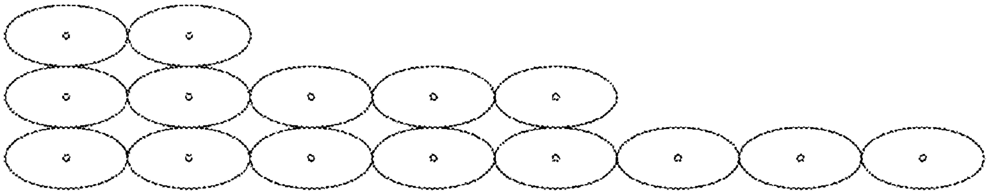
FIG. 12 is a side view I of the lobule body in the present application.

In the present embodiment, two kinds of structures that a plurality of lobule layers form a lobule body 2 are provided. As shown in FIG. 11, the number of the lobule layers in the lobule body 2 is three, and the sizes and shapes of the three lobule layers are identical completely in the structure. The present embodiment further provides another structure that the three lobule layers are different in size, and the sizes of the three lobule layers are gradually increased from top to bottom, resulting in a greater thickness of the side (i.e. an interwoven side) close to an outer layer fabric 12, and a smaller thickness of the side (i.e. a free side) away from the outer layer fabric 12, as shown in FIG. 12.

The difference of the above-mentioned preparation method of the lobule body and the preparation method in embodiment 1 lies in that, in step 2 in embodiment 1, three groups of grab ropes 3 are disposed, three layers of inner side wefts 22 are respectively formed between the outer layer fabric 12 and each of the grab ropes 13, and there are specifically two preparation methods. For the first method, during weaving, firstly, simultaneous weaving is performed on the outer layer fabric 12 to form three layers of inner side wefts 22; then, layer-by-layer interweaving is performed on the inner side wefts 22 to form inner side warps 21; and when the inner side warps 21 are interwoven to the edges of the inner side wefts 22, a thread end of each of the inner side warps 21 is interwoven with the inner side weft 22 on an adjacent layer to form seamless connection. For the second method, during weaving, firstly, weaving is performed on the outer layer fabric 12 to form a layer of inner side weft 22; interweaving is performed on the inner side weft 22 to form an inner side warp 21; the thread end of the inner side warp 21 returns to a location where the outer layer fabric 12 is interwoven so as to be ligated after being sequentially overlocked on the free side of the lobule layer, and thus, a first lobule layer is formed; and then, the above-mentioned steps are repeated to form a second lobule layer and a third lobule layer. The difference of the preparation processes of the second lobule layer and the third lobule layer and the preparation process of the first lobule layer lies in that the thread end of the inner side warp 21 is also interwoven with the inner side weft 22 of the adjacent lobule layer when being sequentially overlocked on the free side of the inner side weft 22 to form seamless connection.

Obviously, the above-mentioned embodiments are merely intended to clearly describe examples, rather than to limit implementations. Those of ordinary skill in the art can also make other variations or alterations in different forms on the basis of the above-mentioned description. It is unnecessary and impossible to exhaustively list all the implementations herein. Apparent variations or alterations derived therefrom still fall within the protection scope of the present application.

What is claimed is:

1. A heart valve prosthesis, comprising a support element of a tubular structure, and at least two lobule bodies connected to the inner wall of the support element, wherein the support element comprises an outer layer fabric having selvages on two opposite sides, and a suture line for fixing the other two sides of the outer layer fabric to each other to form the tubular structure;

each of the lobule bodies is formed by stacking at least one lobule layer; and two opposite sides of the lobule body are respectively an interwoven side and a free side, with the interwoven side being fixed between the two selvages of the outer layer fabric by means of weaving, and the free side being a selvage;

wherein each of the lobule layers is formed by interweaving an inner side warp and an inner side weft; the interwoven side of the lobule body is fixed by means of weaving the inner side weft of each of the lobule layers onto the outer layer fabric; and the inner side warp is woven on the inner side weft;

wherein the number of yarns forming the inner side weft of each of the lobule layers is one; and the number of yarns forming the inner side warp of each of the lobule layers is also set to be one.

2. The heart valve prosthesis of claim 1, wherein the number of yarns forming the inner side weft in each of the lobule bodies is not greater than the number of the lobule layers in each of the lobule bodies; or/and the number of yarns forming the inner side warp in each of the lobule bodies is not greater than the number of the lobule layers in each of the lobule bodies.

3. The heart valve prosthesis of claim 1, wherein the number of yarns forming all the inner side wefts in all the lobule bodies is not greater than the number of the lobule bodies; or/and the number of yarns forming all the inner side warps in all the lobule bodies is not greater than the number of the lobule bodies.

4. The heart valve prosthesis of claim 3, wherein the number of yarns forming all the inner side warps in all the lobule bodies is set to be one, or/and the number of yarns forming all the inner side wefts in all the lobule bodies is set to be one.

5. The heart valve prosthesis of claim 1, wherein the number of yarns forming the inner side warps and the inner side wefts is set to be one in total.

6. The heart valve prosthesis of claim 1, wherein an interweaving area between each of the lobule bodies and the outer layer fabric is arc-shaped, rectilinear or/and of an irregular geometrical shape on a plane of the outer layer fabric.

7. The heart valve prosthesis of claim 1, wherein the support element and/or the lobule bodies are made of a biocompatible polymer.

8. The heart valve prosthesis of claim 1, wherein the lobule bodies are made of one or more of UHMWPE, PET, PEEK, TPU, PGA, PLGA, PLA, PLLA'S, PDO, PHA's, and PGSU.

9. The heart valve prosthesis of claim 1, wherein the support element is made of one or more of UHMWPE, PET, PEEK, TPU, PGA, PLGA, PLA, PLLA'S, PDO, PHA's, and PGSU.

10. The heart valve prosthesis of claim 1, wherein the length of the support element in the axial direction is 1 mm to 50 mm, and the yarns forming the outer layer fabric have the sizes of 5-100 D.

11. The heart valve prosthesis of claim 1, wherein the number of yarns forming the inner side weft in each of the lobule bodies is not greater than the number of the lobule layers in each of the lobule bodies; or/and the number of yarns forming the inner side warp in each of the lobule bodies is not greater than the number of the lobule layers in each of the lobule bodies.

12. The heart valve prosthesis of claim 2, wherein the number of yarns forming all the inner side wefts in all the lobule bodies is not greater than the number of the lobule bodies; or/and the number of yarns forming all the inner side warps in all the lobule bodies is not greater than the number of the lobule bodies.

13. The heart valve prosthesis of claim 1, wherein the number of yarns forming the inner side warps and the inner side wefts is set to be one in total.

14. The heart valve prosthesis of claim 1, wherein an interweaving area between each of the lobule bodies and the outer layer fabric is arc-shaped, rectilinear or/and of an irregular geometrical shape on a plane of the outer layer fabric.

15. A preparation method for the heart valve prosthesis of claim 1, comprising:

step 1, adopting a plurality of yarns to be arranged to form outer side warps, and adopting one yarn as an outer side weft to be interwoven with the outer side warps to form an outer layer fabric, two opposite sides, parallel to the outer side warps, of the outer layer fabric forming selvages;

step 2, disposing a plurality of grab ropes above the outer layer fabric, providing an interweaving area on the outer layer fabric, selecting one yarn to be interwoven with at least one outer side warp on one side of the interweaving area firstly, then extending to one of the grab ropes where the yarn is fixed, and then returning to the interweaving area, wherein the process of fixation between the interweaving area and one of the grab ropes is repeated until the yarn forms an inner side weft of each lobule layer after the yarn completes all areas from one side of the interweaving area to one side of each of the grab ropes;

step 3, adopting another yarn as an inner side warp to be interwoven on the inner side weft to form an inner side warp of each of the lobule layers; and using a thread end of the inner side warp to weave a plurality of lobule layers into a whole on a free side of the inner side weft to form individual lobule bodies; and step 4, after all the lobule bodies are woven completely, suturing two axial ends of each of the outer side warps on the outer layer fabric by using a suture line.

16. The preparation method of claim 15, wherein in step 3, the thread end of the inner side warp returns to a location adjacent to the interweaving area so as to be ligated after being sequentially overlocked with the inner side weft on the free side of the inner side weft.

17. A preparation method for the heart valve prosthesis of claim 1, comprising:

step 1, adopting a plurality of yarns to be arranged to form outer side warps, providing an interweaving area on the outer side warps, disposing a plurality of grab ropes above the outer side warps, adopting one yarn as an outer side weft to be interwoven with the outer side warps, fixing the yarn forming the outer side weft to one of the grab ropes when being interwoven to the interweaving area, and then, returning the yarn to the interweaving area so as to be further interwoven with the outer side warps; making the yarn forming the outer side weft cooperate with the outer side warps to form an outer layer fabric, fixing the yarn forming the outer side weft to one of the grab ropes after extending to one of the grab ropes when being in the interweaving area, and then, returning the yarn to the outer side warps so that the yarn forming the outer side weft forms an inner side weft at segments between each of the outer side warps and each of the grab ropes;

step 2, adopting another yarn as an inner side warp to be interwoven on the inner side weft to form an inner side warp of each of lobule layers; and using a thread end of the inner side warp to weave a plurality of lobule layers into a whole on a free side of the inner side weft to form individual lobule bodies; and step 3, after all the lobule bodies are woven completely, suturing two axial ends of each of the outer side warps on the outer layer fabric by using a suture line.

18. An artificial valve, comprising a heart valve prosthesis, the heart valve prosthesis including a support element of a tubular structure, and at least two lobule bodies connected to the inner wall of the support element, wherein the support element comprises an outer layer fabric having selvages on two opposite sides, and a suture line for fixing the other two sides of the outer layer fabric to each other to form the tubular structure;

each of the lobule bodies is formed by stacking at least one lobule layer; and two opposite sides of the lobule body are respectively an interwoven side and a free side, with the interwoven side being fixed between the two selvages of the outer layer fabric by means of weaving, and the free side being a selvage;

the heart valve prosthesis prepared by using the preparation method for the heart valve prosthesis of claim 15.

19. The artificial valve of claim 18, further comprising a stent mounted on the heart valve prosthesis.

* * * * *